United States Patent
Vija

(10) Patent No.: US 7,465,929 B2
(45) Date of Patent: Dec. 16, 2008

(54) TRACKING REGION-OF-INTEREST IN NUCLEAR MEDICAL IMAGING AND AUTOMATIC DETECTOR HEAD POSITION ADJUSTMENT BASED THEREON

(75) Inventor: A. Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 129 days.

(21) Appl. No.: 11/799,545

(22) Filed: May 2, 2007

(65) Prior Publication Data

US 2008/0272304 A1 Nov. 6, 2008

(51) Int. Cl.
G01T 1/164 (2006.01)

(52) U.S. Cl. .................................... 250/363.04
(58) Field of Classification Search ............ 250/363.04, 250/363.05, 363.08
See application file for complete search history.

(56) References Cited

U.S. PATENT DOCUMENTS 5,304,806 A * 4/1994 Hines et al. ............... 250/369
6,147,353 A * 11/2000 Gagnon et al. ......... 250/363.05

* cited by examiner

Primary Examiner—Constantine Hannaher
(74) Attorney, Agent, or Firm—Peter L. Kendall

(57) ABSTRACT

A method and system for automatically identifying and tracking a ROI over all planar acquisition view angles of a nuclear imaging system, such as a gamma camera used for SPECT or planar imaging. Temporal intensity variation in emission projection imaging is measured to identify a region of interest (ROI) such as the myocardium. The method automatically tracks the location of the ROI over different planar view angles and adapts detector head orbit and positioning to bring the ROI within a predefined preferred area or so-called "sweet spot" within the FOV of a collimator attached to the front of a scintillation detector surface. After initial positioning of the detector head by the user, the system automatically tracks the ROI location as the detector head(s) rotate about the patient and re-position the detector head(s) appropriately to maintain the ROI within the optimal collimation area of the detector FOV.

17 Claims, 4 Drawing Sheets

TRACKING REGION-OF-INTEREST IN NUCLEAR MEDICAL IMAGING AND AUTOMATIC DETECTOR HEAD POSITION ADJUSTMENT BASED THEREON

FIELD OF THE INVENTION

The present invention generally relates to nuclear medicine, and systems for obtaining nuclear medicine images. In particular, the present invention relates to a method and apparatus for identifying a region-of-interest (ROI) in a nuclear medical image scan, such as an organ or particular region of a patient undergoing imaging, and automatically tracking the identified ROI over different view angles and adjusting detector head positioning so that the identified ROI remains in an optimal area of the field of view (FOV) of the detector head, in particular with respect to a particular collimator being used in the imaging application.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body. One or more detectors are used to detect the emitted gamma photons, and the information collected from the detectors is processed to calculate the position of origin of the emitted photon from the source (i.e., the body organ or tissue under study). The accumulation of a large number of detected gamma positions allows an image of the organ or tissue under study to be displayed.

In certain nuclear tomographic imaging techniques, such as Single Photon Emission Computed Tomography (SPECT), events are detected by one or more collimated radiation detectors, also referred to as gamma cameras, which are typically rotated about a patient's body in a defined orbital path. The collimators employed with such detectors have apertures running through the body of the collimator to assure that only gamma photons traveling along specific paths aligned with the holes will pass through to the detector. Upon detection of a gamma ray, it is inferred that the gamma ray then came along the same path that the collimator hole is directed.

Collimator design conventionally is non-adaptive, meaning that the design of the collimator with respect to length, septa, dimensions and focal or parallel nature of the collimator holes cannot be adjusted. Therefore, if different resolution and sensitivity is desired, the collimator needs to be replaced with another collimator having different dimensions and focal characteristics. For example, in some imaging applications a single or multi-focal collimator should be used, while in other applications a parallel hole collimator should be used. Each different design of collimator may have a different optimal region or so-called "sweet spot" within its FOV in which the ROI of an imaged object should remain for optimal results.

FIG. 1 illustrates one example of a prior art focusing collimator. The focusing collimator 2 contains a number of channels 4 separated by septa 10. The channels 4 are all aimed at a common focal point 6. The collimator thus receives a "fan beam" 8 of radiation emitted from focal point 6. Consequently, it is desirable in imaging applications using such a focusing collimator to maintain the ROI centered at focal point 6 in the FOV of the collimator.

In SPECT as well as planar imaging, image scanning consists of multiple image data acquisitions taken over multiple planar view angles with respect to the patient. Frequently, the target organ (e.g., the heart) or the ROI has to be positioned with respect to the detector head so that it remains within an optimal collimation area within the FOV of the detector, which varies depending on the design of the collimator (e.g. whether the collimator is a focusing collimator, multi-focal collimator, parallel hole collimator, etc.).

FIG. 2 illustrates a typical scenario with respect to a target organ 201, a FOV 202, and a "sweet spot" or optimal imaging area 203 within the FOV 202. Conventionally, the initial detector head positioning is done manually by a technician based on only a few views. Thus, for example, for view angle 1, the target organ is optimally positioned within the sweet spot 203 of the collimator FOV 202; however for view angle N, which corresponds to a position of the detector head that is rotated with respect to the initial position of the detector head for view angle 1, the target organ 201 is outside the sweet spot 203 (while continuing to be within the overall FOV 202). In this case, sub-optimal image data will be acquired from view angle N. To avoid this result, it would be necessary for the technician to make manual adjustments at each different view angle, which would be time consuming and not necessarily consistent from view to view. Accordingly, there exists a need for improvement in the art with respect to maintaining a target organ or ROI within an optimal imaging area of a FOV of a detector head over all view angles.

SUMMARY OF THE INVENTION

The present invention solves the problems in the prior art by providing a method and system for automatically identifying and tracking a ROI over all planar acquisition view angles. The invention introduces the concept of measuring temporal intensity variation in emission projection imaging to identify a ROI (such as the myocardium). The method automatically tracks the location of the ROI over different planar view angles and adapts detector head orbit and positioning to bring the ROI within a predefined preferred area or so-called "sweet spot" within the FOV of a collimator attached to the front of a scintillation detector surface. After initial positioning of the detector head by the user, the system automatically tracks the ROI location as the detector head(s) rotate about the patient and re-position the detector head(s) appropriately to maintain the ROI within the optimal collimation area of the detector FOV.

DETAILED DESCRIPTION OF THE PREFERRED EMBODIMENTS

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

The invention is based on the fact that the dynamic "wash-in" and "wash-out" of a radiopharmaceutical into tissue, as well as natural organ motion such as the beating of the heart or the movement of the diaphragm during respiration, respectively gives rise to a concentration change in tissue or to a positional change of radioactive concentration c. Thus, in general the radioactive concentration c can be expressed as a function of position and time, or $c=c(\vec{r}, t)$, where $\vec{r}$ denotes a position vector and t denotes a time variable.

To generalize further, consider all other possible effects in addition to radiation concentration that would cause image intensity variations at location $\vec{r}$ as being described by a function $I(\vec{r}, t)$. Then, in accordance with the invention, an image data acquisition is set up (which may be a dynamic acquisition, a gated acquisition, a listmode acquisition, etc.), which acquires image data in a $\Delta t$ time interval so that the variation of $I(\vec{r}, t)$ can be measured. The measurement is made by fulfilling well-known temporal sampling criteria.

The acquired image data is subsequently analyzed to identify pixels that satisfy preselected intensity signature conditions, which may be characterized a priori or selected by a user. Any method that can detect intensity variation from image frame to image frame, such as difference filtering, can be used to identify certain pixels of interest.

Using well-known techniques, the pixels meeting the preselected intensity variation conditions can be bounded by a simple convex bounding area. This bounding area then is used to analyze whether the ROI or target organ is within a predefined preferred imaging area within the FOV of the collimator (detector). Such predefined imaging area can be simply expressed in terms of an FOV coordinate system.

Then, as the view angle is changed by rotation or motion of the detector head and the location of the target organ or ROI moves in the coordinate system of the FOV, the encompassing convex bounding area moves similarly. Consequently, the location of the target organ or ROI is automatically tracked, and this positional information can be used to adjust the scan motion accordingly, so that for example the target organ remains in the desired imaging area or "sweet spot" within the FOV.

Figure 1:
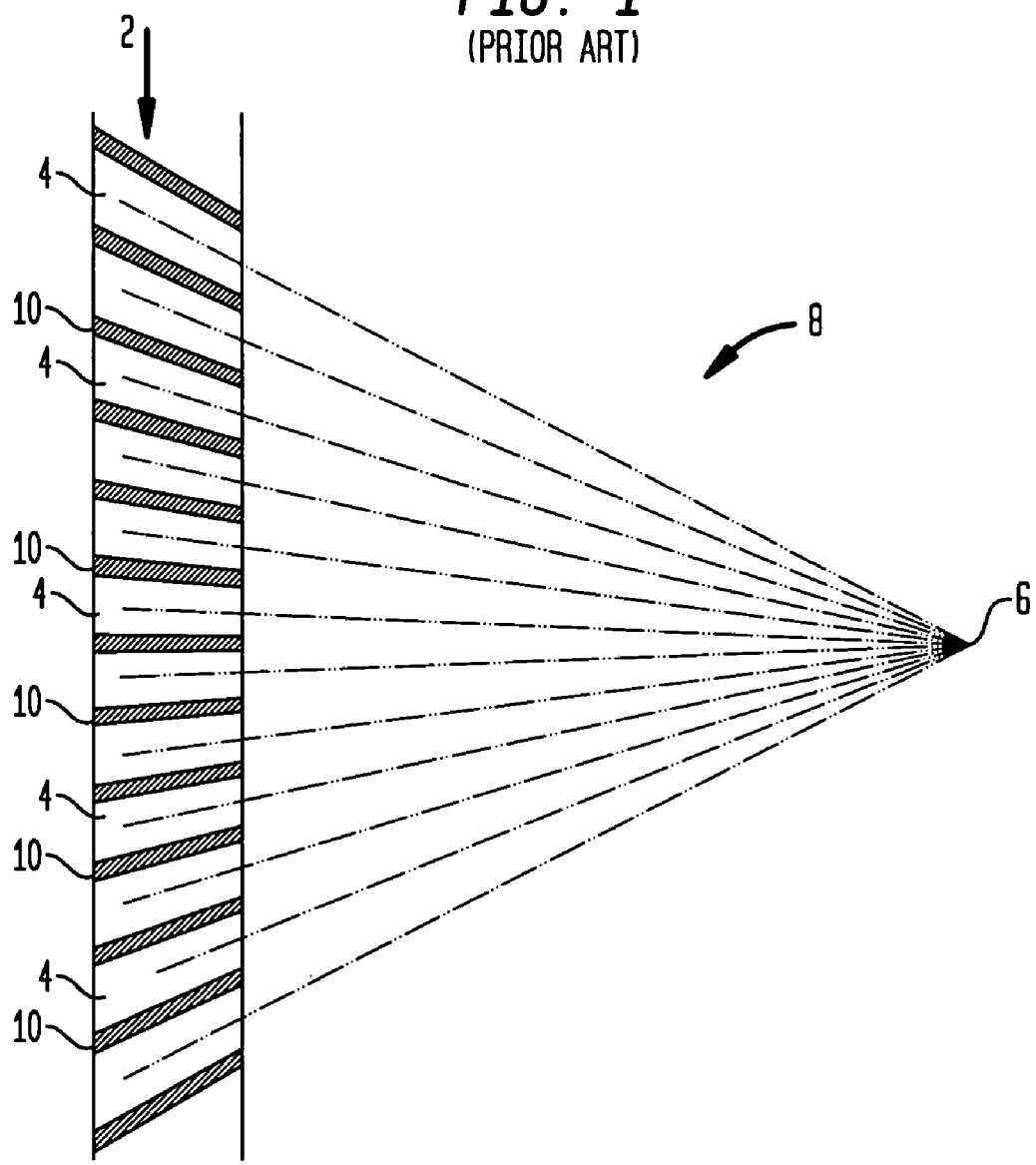
FIG. 1 is a cross-sectional view of an example focusing collimator having a preferred imaging area or "sweet spot," which is applicable to the present invention.
Figure 2:
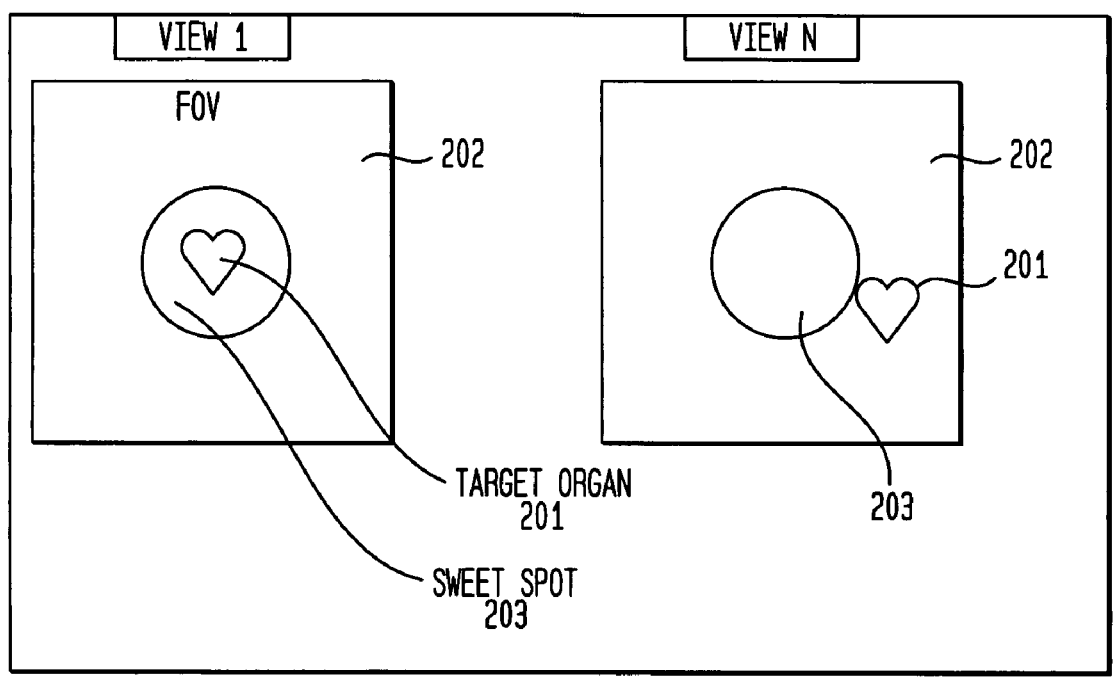
FIG. 2 illustrates examples of possible loss of optimal ROI location within the FOV of a collimated detector as the detector rotates about a patient.
Figure 3:
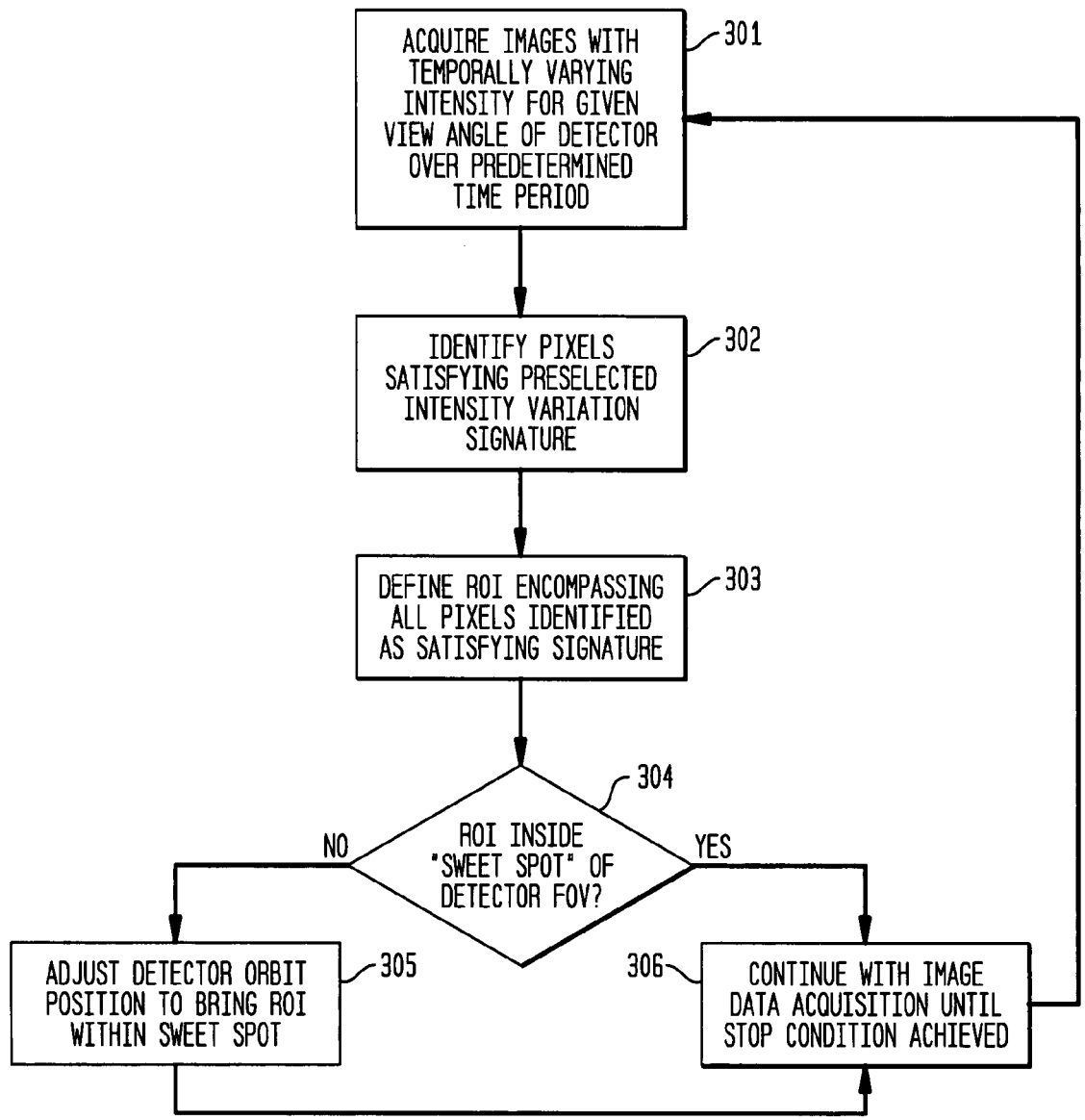
FIG. 3 is a flow diagram of a method in accordance with one embodiment of the invention.

FIG. 3 illustrates a method of identifying and tracking a ROI of a patient undergoing nuclear medical imaging in accordance with an embodiment of the invention. At step 301, planar projection images are acquired at a particular view angle over a certain time interval, which images vary temporally in intensity as a result of either organ motion or "wash-in" and "wash-out" of radiopharmaceutical concentration. At step 302, the acquired image data is analyzed to identify pixels that satisfy a preselected intensity variation signature. At step 303, a ROI is defined so as to encompass all of the pixels identified in step 302. Then at step 304, the location of the ROI in FOV coordinates is compared with the location of the "sweet spot" also in FOV coordinates, to determine whether the ROI is inside the sweet spot or preferred imaging area within the FOV.

If not, then at step 305 the detector orbit position is adjusted in accordance with the difference between the position of the ROI and the position of the sweet spot, to bring the ROI back within the sweet spot. Image data acquisition then continues at step 306 until a "stop" condition is achieved, such as a predefined acquisition time having elapsed or a predefined number of interaction events being accumulated. The detector head(s) are then rotated to the next view angle, and the process returns to step 301. On the other hand, if the ROI is already within the sweet spot as determined in step 304, the process immediately proceeds with image data acquisition at step 306.

Figure 4:
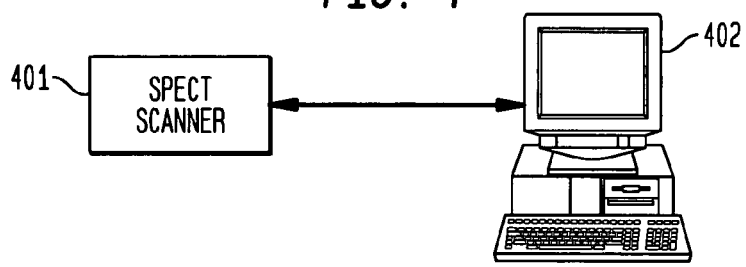
FIG. 4 is a diagram illustrating a SPECT scanner and processor system in accordance with another aspect of the invention.

FIG. 4 illustrates a system for carrying out the invention. The system includes a SPECT scanner 401 and a processing system 402. The processing system 402 controls the operation of the SPECT scanner, including the rotation and motion of detector heads, receives image and other data from the SPECT scanner, and processes data from the scanner. The procedure illustrated in FIG. 3 may be implemented as software or firmware in the processing system 402.

Figure 5:
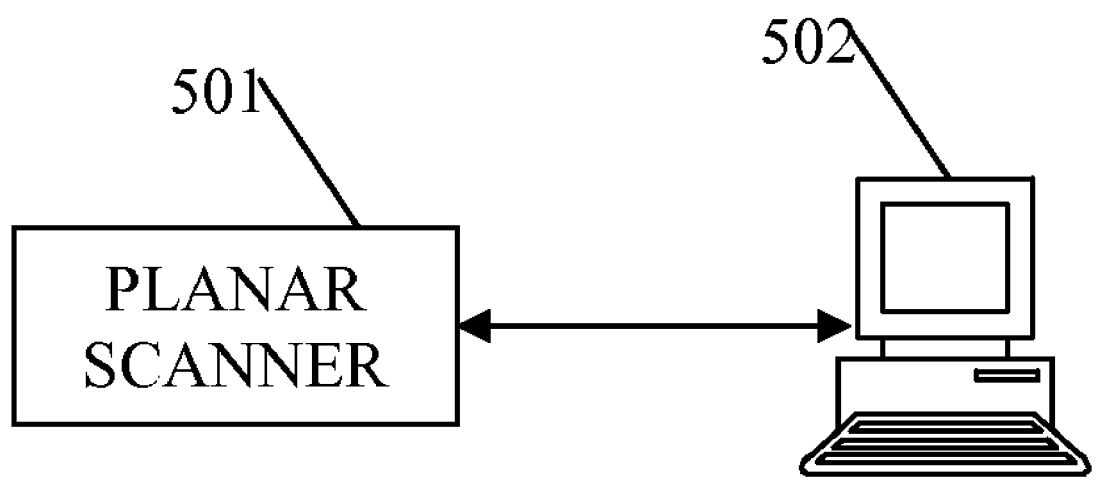
FIG. 5 is a diagram illustrating as SPECT scanner and processor system in accordance with yet another aspect of the invention.

FIG. 5 illustrates another system for carrying out the invention. The system includes a planar scanner 501 and a processing system 502. The processing system 502 controls the operation of the planar scanner, including the rotation and motion of detector heads, receives image and other data from the planar scanner, and processes data from the scanner. The procedure illustrated in FIG. 3 may be implemented as software or firmware in the processing system 502.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

The invention claimed is:

1. A method of identifying and tracking a region of interest in a patient undergoing medical imaging by a nuclear imaging apparatus, comprising:
    acquiring image data of said patient over a predefined time interval at a particular view angle;
    identifying elements of said image data that satisfy a preselected intensity variation signature over said time interval;
    defining a bounding area encompassing all identified elements satisfying said preselected intensity variation signature; and
    comparing said bounding area with a predefined preferred imaging area within a field of view of said nuclear imaging apparatus and identifying a positional difference between said bounding area and said preferred imaging area.

2. The method of claim 1, further comprising the step of adjusting a detector of said nuclear imaging apparatus based on said identified difference so as to bring said bounding area within said preferred imaging area.

3. The method of claim 2, further comprising the step of acquiring image data for image reconstruction after adjusting said detector.

4. The method of claim 2, wherein the step of adjusting comprises adjusting a detector orbit about said patient.

5. The method of claim 1, wherein identified elements of said image data comprise image pixels.

6. The method of claim 1, wherein the step of identifying elements of said image data comprises using a difference filter between different temporal frames of image data.

7. The method of claim 1, further comprising defining said preferred imaging area as a function of a particular collimator attached to said nuclear imaging apparatus.

8. A nuclear imaging apparatus, comprising:
   a scanner system; and
   a processor coupled to receive image data from and to control operation of said scanner system, said processor containing instructions causing said apparatus to acquire image data of a patient over a predefined time interval at a particular view angle;
   identify elements of said image data that satisfy a preselected intensity variation signature over said time interval;
   define a bounding area encompassing all identified elements satisfying said preselected intensity variation signature; and
   compare said bounding area with a predefined preferred imaging area within a field of view of said nuclear imaging apparatus and identify a positional difference between said bounding area and said preferred imaging area.

9. The apparatus of claim 8, wherein said processor further contains instructions causing said processor to adjust a detector of said nuclear imaging apparatus based on said identified difference so as to bring said bounding area within said preferred imaging area.

10. The apparatus of claim 9, wherein said processor further contains instructions causing said scanner system to acquire image data for image reconstruction after adjusting said detector.

11. The apparatus of claim 9, wherein said processor adjusts a detector orbit about said patient.

12. The apparatus of claim 8, wherein identified elements of said image data comprise image pixels.

13. The apparatus of claim 8, wherein said processor uses a difference filter between different temporal frames of image data to identify elements of said image data that satisfy said intensity variation signature.

14. The apparatus of claim 8, wherein said preferred imaging area is defined as a function of a particular collimator attached to said nuclear imaging apparatus.

15. The apparatus of claim 8, further comprising a focusing collimator attached to said scanner system.

16. The apparatus of claim 8, wherein said scanner system is a SPECT system.

17. The apparatus of claim 8, wherein said scanner system is a planar imaging system.

* * * * *